(12) United States Patent
Matsuda et al.

(10) Patent No.: US 8,759,566 B2
(45) Date of Patent: Jun. 24, 2014

(54) METHOD FOR PRODUCING α-HYDROXYCARBOXYLIC ACID ESTER

(75) Inventors: Hideho Matsuda, Niigata (JP); Yuuichi Sugano, Niigata (JP); Yoshikazu Shima, Niigata (JP); Masaki Takemoto, Niigata (JP); Genki Nogami, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 118 days.

(21) Appl. No.: 13/259,156

(22) PCT Filed: Mar. 30, 2010

(86) PCT No.: PCT/JP2010/055738
§ 371 (c)(1),
(2), (4) Date: Dec. 6, 2011

(87) PCT Pub. No.: WO2010/113964
PCT Pub. Date: Oct. 7, 2010

(65) Prior Publication Data
US 2012/0095253 A1    Apr. 19, 2012

(30) Foreign Application Priority Data

Apr. 3, 2009    (JP) .................................. 2009-091389

(51) Int. Cl.
*C07C 69/66*    (2006.01)

(52) U.S. Cl.
USPC ........................................................ 560/179

(58) Field of Classification Search
CPC ...... C07C 67/08; C07C 69/68; C07C 69/734; C07C 255/00; C07C 67/343; C07C 69/75; C07C 69/675; C07C 2101/14; C07C 51/36; C07C 51/06; C07C 51/265; C07C 2101/02; C07C 209/56
USPC ............ 560/179, 181, 1; 562/400; 564/1, 123
See application file for complete search history.

(56) References Cited

U.S. PATENT DOCUMENTS

| 4,464,539 A | * | 8/1984 | Hashimoto et al. ........... 560/212 |
| 4,973,739 A | | 11/1990 | Nagasawa et al. |
| 2009/0209781 A1 | | 8/2009 | Ackermann et al. |

FOREIGN PATENT DOCUMENTS

| EP | 0 342 475 A1 | 11/1989 |
| JP | 57 67534 | 4/1982 |
| JP | 58 055444 | 4/1983 |
| JP | 1 290651 | 11/1989 |
| JP | 06 345692 | 12/1994 |
| JP | 07 258154 | 10/1995 |
| JP | 8-73406 A | 3/1996 |
| JP | 08 268964 | 10/1996 |
| JP | 169432 A | * 6/2000 |
| WO | WO 2008/009503 A1 | 1/2008 |

OTHER PUBLICATIONS

JP169432A (2000) (machine translation conducted on the website titled AIPN Japan Patent Office on Apr. 2, 2013).*
Extended European Search Report Issued Nov. 9, 2012 in Patent Application No. 10758735.4.
International Search Report Issued Apr. 27, 2010 in PCT/JP10/055738 Filed Mar. 30, 2010.

* cited by examiner

*Primary Examiner* — Brandon Fetterolf
*Assistant Examiner* — Blaine G Doletski
(74) *Attorney, Agent, or Firm* — Oblon, Spivak, McClelland, Maier & Neustadt, L.L.P.

(57) ABSTRACT

Provided is a process for producing α-hydroxycarboxylic esters from α-hydroxycarboxylic amides and aliphatic alcohols, wherein it is a production process which is inhibited in a production cost and enhanced in a conversion rate and a selectivity and which is industrially advantageous. To be specific, it is a production process for α-hydroxycarboxylic ester characterized by subjecting α-hydroxycarboxylic amide and aliphatic alcohol to a gas phase reaction in the presence of a zirconium dioxide catalyst. A catalyst lifetime is improved to a large extent by using a zirconium dioxide catalyst containing a specific element.

20 Claims, No Drawings

METHOD FOR PRODUCING α-HYDROXYCARBOXYLIC ACID ESTER

CROSS-REFERENCE TO RELATED APPLICATIONS

This application is a National Stage of PCT/JP2010/055738 filed on Mar. 30, 2010. This application is based upon and claims the benefit of priority to Japanese Application No. 2009-091389 filed on Apr. 3, 2009.

BACKGROUND OF THE INVENTION

1. Field of the Invention

The present invention relates to a process for producing α-hydroxycarboxylic esters from α-hydroxycarboxylic amide and aliphatic alcohols.

2. Background of the Invention

A process in which alcohol is reacted with nitrile under the presence of an acid catalyst is known as a process for producing α-hydroxycarboxylic esters from a long time ago. For example, a process in which lactonitrile is dissolved in alcohol and water, in which sulfuric acid is added to hydrolyze and esterify it and in which alcohol steam is introduced into the reaction mixture obtained is disclosed as a process for producing lactic esters (refer to patent documents 1 and 2). Further, a process in which acetone cyanhydrin is reacted with alcohol in the presence of an acid catalyst is known as a process for producing α-hydroxyisobutyric esters (refer to patent documents 3 and 4).

Further, various processes have so far been proposed as a process for producing α-hydroxycarboxylic esters from α-hydroxycarboxylic amides and aliphatic alcohols. In a case of, for example, a liquid phase reaction, known are processes in which α-hydroxyisobutyroamide or lactoamide is reacted with alcohols in the presence of metal alkoxide, an insoluble solid acid catalyst, a soluble metal complex containing titanium and/or tin and α-hydroxycarboxylic amide as constitutional components or a trifluoromethanesulfonic acid metal salt as a catalyst (refer to patent documents 5 to 11).

Patent document 1: Japanese Patent Publication No. 8061/1955
Patent document 2: Japanese Patent Publication No. 2333/1965
Patent document 3: U.S. Pat. No. 2,041,820
Patent document 4: Japanese Patent Application Laid-Open No. 230241/1992
Patent document 5: Japanese Patent Application Laid-Open No. 3015/1977
Patent document 6: Japanese Patent No. 3222639
Patent document 7: Japanese Patent Application Laid-Open No. 258154/1995
Patent document 8: Japanese Patent Application Laid-Open No. 279120/1999
Patent document 9: Japanese Patent Application Laid-Open No. 26370/2000
Patent document 10: Japanese Patent Application Laid-Open No. 292824/1999
Patent document 11: Japanese Patent Application Laid-Open No. 169432/2000

SUMMARY OF THE INVENTION

The processes disclosed in the patent documents 1 to 4 are processes which are increased in production costs in terms of requiring a large amount of the acid catalysts, necessitating a reaction equipment using a corrosion resistant material for making it possible to use the above acid catalysts, needing large amounts of energy and cost in order to recover and reuse the unreacted raw materials and by-produced ammonia and making it necessary to dispose unnecessary compounds such as ammonium sulfate and the like produced in large amounts, and they have room of further improvement before carried out industrially.

Also, the reactions disclosed in the patent documents 5 to 11 are equilibrium reactions, and ammonia produced in the reactions has to be discharged to an outside of the systems in order to enhance the conversion rates of the raw materials. Various proposals are made on the above matter, but any of the processes used requires large amounts of energy and cost for recovering ammonia and alcohols, and they are not necessarily industrially excellent processes from an economical viewpoint.

The present invention has been made under the situations described above, and an object of the present invention is to provide a process for producing α-hydroxycarboxylic esters from α-hydroxycarboxylic amide and aliphatic alcohols, wherein it is a production process which is inhibited in a production cost and enhanced in a conversion rate and a selectivity and which is industrially advantageous.

Intensive investigations repeated by the present inventors in order to achieve the object described above have resulted in finding that the high conversion rate is obtained as compared with a liquid phase reaction by subjecting α-hydroxycarboxylic amide and aliphatic alcohols to a gas phase reaction in the presence of a zirconium dioxide catalyst, and it has been found that this makes it possible to efficiently produce α-hydroxycarboxylic esters. Further, they have found that use of a zirconium catalyst containing a specific element makes it possible to enhance a lifetime of the catalyst to a large extent. The present invention has been completed based on the above knowledges.

That is, the present invention relates to the following items (1) to (7).

(1) A production process for α-hydroxycarboxylic ester characterized by subjecting α-hydroxycarboxylic amide and aliphatic alcohol to a gas phase reaction in the presence of a zirconium dioxide catalyst.

(2) The production process for α-hydroxycarboxylic ester according to the above item (1), wherein the zirconium dioxide catalyst contains at least one element selected from 2nd to 4th groups, a 7th group and 9th to 13th groups in the periodic table, lanthanoid, antimony (Sb) and bismuth (Bi).

(3) The production process for α-hydroxycarboxylic ester according to the above item (1), wherein the zirconium dioxide catalyst contains at least one element selected from boron (B), aluminum (Al), manganese (Mn), cobalt (Co), nickel (Ni), yttrium (Y), lanthanum (La) and ytterbium (Yb).

(4) The production process for α-hydroxycarboxylic ester according to any one of the above items (1) to (3), wherein the α-hydroxycarboxylic amide is represented by the following Formula (I):

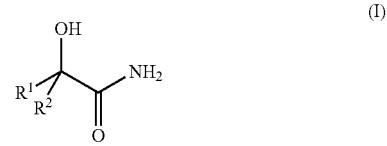

(wherein $R^1$ and $R^2$ each represent independently a hydrogen atom, an alkyl group having 1 to 20 carbon atoms, an alkenyl group having 2 to 20 carbon atoms or a cycloalkyl group having 3 to 20 ring-forming carbon atoms), and the aliphatic alcohol is represented by $R^3OH$ (wherein $R^3$ represents an alkyl group having 1 to 20 carbon atoms, an alkenyl group having 2 to 20 carbon atoms or a cycloalkyl group having 3 to 20 ring-forming carbon atoms).

(5) The production process for α-hydroxycarboxylic ester according to any one of the above items (1) to (3), wherein the α-hydroxycarboxylic amide is lactoamide or α-hydroxyisobutyroamide.

(6) The production process for α-hydroxycarboxylic ester according to any one of the above items (1) to (5), wherein the aliphatic alcohol is methanol or ethanol.

(7) The production process for α-hydroxycarboxylic ester according to any one of the above items (1) to (6), wherein a reaction temperature is 150 to 270° C., and a reaction pressure is 1 to 300 kPa.

According to the production process of the present invention, by-products such as ammonium sulfate which cost a lot of expenses for disposing are not produced. Further, since the high conversion rate is obtained in the present invention as compared with a case of a liquid phase reaction, by-produced ammonia does not have to be discharged to an outside of the system together with the solvent, and an energy cost for volatilizing the solvent in the reaction can be saved. Further, according to the present inventors, α-hydroxycarboxylic esters can be produced at a high selectivity.

BEST MODE FOR CARRYING OUT THE INVENTION

Production Process for α-Hydroxycarboxylic Ester:

The present invention relates to a production process for α-hydroxycarboxylic ester characterized by subjecting α-hydroxycarboxylic amide and aliphatic alcohol to a gas phase reaction in the presence of a zirconium dioxide catalyst.

Zirconium Dioxide Catalyst:

The zirconium dioxide catalyst is used as a catalyst in the present invention. From the viewpoint of enhancing a catalyst lifetime, preferably used is the zirconium dioxide catalyst containing at least one element (hereinafter referred to as the added element) selected from 2nd to 4th groups, a 7th group and 9th to 13th groups in the periodic table, lanthanoid, antimony (Sb) and bismuth (Bi). The above added element is more preferably, from the viewpoint of enhancing the catalyst lifetime, elements of a 3rd group, a 7th group, a 9th group, a 10th group and a 13th group in the periodic table, further preferably boron (B), aluminum (Al), manganese (Mn), cobalt (Co), nickel (Ni), yttrium (Y), lanthanum (La) and ytterbium (Yb). Other elements excluding the above added elements may be contained, and a content thereof is, from the viewpoint of the conversion rate and the selectivity, preferably 30% by mass or less, more preferably 15% by mass or less and further preferably 5% by mass or less based on the added element.

When the zirconium dioxide catalyst contains the added element described above, a content of the added element is, from the viewpoint of enhancing the catalyst lifetime, 0.1 to 30% by mole, more preferably 0.5 to 10% by mole, further preferably 1 to 8% by mole and particularly preferably 1 to 7% by mole based on a total of zirconium and the added element.

Commercial products may be used for the zirconium dioxide catalyst or prepared products may be used. Also, zirconium dioxide or zirconium dioxide hydrate obtained by suitably washing a zirconium hydroxide catalyst with water, drying it and then burning it can be used as well for the zirconium dioxide catalyst. Further, zirconium dioxide containing zirconium hydroxide can be used as well for the zirconium dioxide catalyst.

The commercial products of the zirconium dioxide catalyst or a zirconium hydroxide catalyst which is a precursor thereof include, for example, "XZO1501" series, "XZO632" series and "XZO882" series manufactured by MEL Chemicals Inc. and "NN zirconium hydroxide", "R zirconium hydroxide", "RS zirconium hydroxide" and "RSC-HP" (all trade names) manufactured by Daiichi Kigennso Kagaku Kogyo Co., Ltd.

The zirconium dioxide catalyst which is controlled to a size of preferably 3.5 to 40 mesh, more preferably 5 to 30 mesh is preferably used from the viewpoints of a conversion rate and a selectivity and the viewpoint of obtaining the stable reaction results.

Method for Preparing Zirconium Dioxide Catalyst:

A method for preparing the zirconium dioxide catalyst shall not specifically be restricted, and optional methods can be used. The starting raw material can be selected from, for example, a zirconium elemental substance and oxide, hydroxide, chloride, inorganic acid salts and organic acid salts of zirconium. Further, all materials which can be zirconium dioxide or zirconium dioxide hydrate by subjecting to chemical treatment, burning treatment and the like can be used as the starting raw material. To be specific, the above starting raw materials include, for example, zirconium dioxide, zirconium acetylacetonate, zirconium chloride, zirconium oxychloride, zirconium oxynitrate, zirconium isopropoxide, zirconium sulfate and the like.

A precipitation method is used well as the preparing method. To be specific, it is a method in which the raw materials described above such as zirconium oxychloride, zirconium oxynitrate and the like are reacted with alkalis such as ammonia, amine, sodium hydroxide, sodium carbonate, sodium bicarbonate, ammonium carbonate, ammonium bicarbonate and the like to thereby obtain a white precipitate of zirconium hydroxide and in which zirconium hydroxide thus obtained is sufficiently washed with water, then dried and burned to obtain zirconium dioxide hydrate or zirconium dioxide.

A method for adding the added elements described above to the zirconium dioxide catalyst shall not specifically be restricted, and publicly known methods can be used. Capable of being used is, for example, an impregnation method in which zirconium dioxide, zirconium dioxide hydrate or zirconium hydroxide which is commercially available or prepared is impregnated with a salt containing the added element which is turned into a solution state. Further, capable of being used as well is a method in which zirconium dioxide, zirconium dioxide hydrate or zirconium hydroxide which is commercially available or prepared is kneaded with metal oxide, metal hydroxide or a salt containing the added element. Also, a co-precipitation method, a co-gelation method, an ion exchange method and the like can be used as well.

The zirconium dioxide catalyst containing the added element described above can be obtained by subjecting the mixtures obtained by the above methods to burning treatment.

The impregnation method described above can be carried out, to be more specific, by dipping zirconium dioxide, zirconium dioxide hydrate or zirconium hydroxide in a solution obtained by dissolving a supplying source of the added element in advance in a solvent. The above solvent is preferably water. Also, any ones can be used as the supplying source of the added element as long as they are soluble in the solvent used, and, for example, chlorides, nitrates, sulfates, organic acid salts and the like can be used. However, when chlorides and sulfates are used as the supplying source of the element, the halogen ions and the sulfate each remaining in the catalyst have to be removed by sufficiently washing in order to inhibit the selectivity from being deteriorated by the halogen ions and the sulfate which elevate an acidity of the catalyst, and therefore the nitrates and the organic acid salts are particularly preferably used as the supplying source of the element. After impregnated, the solvent is removed, and the solid matter is burned or dried, whereby the targeted zirconium dioxide catalyst can be obtained.

Further, the co-precipitation method described above can be carried out by allowing the supplying source of the element to be present in the reaction system when carrying out an operation of obtaining a white precipitate of zirconium hydroxide in the precipitation method described above. The supplying source of the element is preferably salts which are soluble in water, and, for example, chlorides, nitrates, sulfates, organic acid salts and the like are used. The nitrates and the organic acid salts are preferred because of the same reason as in a case of the impregnation method described above.

"Burning" described above is usually carried out under aerial atmosphere in any cases, but it may be carried out under inert gas atmosphere. The burning temperature is usually 300 to 700° C., preferably 400 to 500° C. in any cases. Usually, the burning time is preferably 1 to 6 hours.

A molding method for the zirconium dioxide catalyst can be carried out by a method known to persons having ordinary skill in the art, and for example, extrusion molding, compression molding and the like can be used. A molding aid can be used in molding, or the catalyst components can be carried on a carrier.

α-Hydroxycarboxylic Amide:

α-Hydroxycarboxylic amide used in the present invention shall not specifically be restricted as long as it is a carboxylic amide compound having a hydroxyl group at an α-position, and from the viewpoint of a usefulness thereof as a raw material for medical products and agricultural chemicals, it is preferably a compound represented by the following Formula (I):

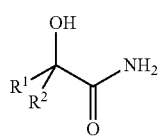

(wherein $R^1$ and $R^2$ each represent independently a hydrogen atom, an alkyl group having 1 to 20 carbon atoms, an alkenyl group having 2 to 20 carbon atoms or a cycloalkyl group having 3 to 20 ring-forming carbon atoms).

The alkyl group having 1 to 20 carbon atoms represented independently by $R^1$ and $R^2$ respectively may be linear or branched and includes, for example, methyl, ethyl, n-propyl, isopropyl, n-butyl, isobutyl, t-butyl, various pentyls ("various" includes linear and all branched structures; hereinafter the same shall apply), various hexyls, various octyls, various decyls, various dodecyls, various tetradecyls, various hexadecyls and the like. From the viewpoints of an easiness in obtaining the raw materials and a usefulness thereof as a raw material for medical products and agricultural chemicals, the above alkyl group is preferably an alkyl group having 1 to 10 carbon atoms, more preferably an alkyl group having 1 to 5 carbon atoms and further preferably methyl.

The alkenyl group having 2 to 20 carbon atoms represented independently by $R^1$ and $R^2$ respectively may be linear or branched and includes, for example, vinyl, various propenyls, various butenyls, various hexenyls, various octenyls, various decenyls, various dodecenyls, various tetradecenyls, various hexadecenyls, various octadecenyls and the like. The above alkenyl group is preferably an alkenyl group having 2 to 10 carbon atoms, more preferably an alkenyl group having 2 to 5 carbon atoms.

The cycloalkyl group having 3 to 20 ring-forming carbon atoms represented independently by $R^1$ and $R^2$ respectively includes, for example, cyclopentyl, cyclooctyl, cycloheptyl, cyclodecyl and the like. The above cycloalkyl group is preferably a cycloalkyl group having 3 to 10 ring-forming carbon atoms, more preferably a cycloalkyl group having 3 to 8 ring-forming carbon atoms.

Among them, both of $R^1$ and $R^2$ are, from the viewpoints of an easiness in obtaining the raw materials and a usefulness thereof as a raw material for medical products and agricultural chemicals, preferably a hydrogen atom or an alkyl group having 1 to 20 carbon atoms, more preferably a hydrogen atom or an alkyl group having 1 to 10 carbon atoms, further preferably a hydrogen atom or an alkyl group having 1 to 5 carbon atoms and particularly preferably a hydrogen atom or methyl. That is, the α-hydroxycarboxylic amide is particularly preferably lactoamide or α-hydroxyisobutyroamide from the same viewpoints as described above.

Aliphatic Alcohol:

The aliphatic alcohol used in the present invention shall not specifically be restricted, and from the viewpoint of a usefulness thereof as a raw material for medical products and agricultural chemicals, it is preferably a compound represented by $R^3OH$ (wherein $R^3$ represents an alkyl group having 1 to 20 carbon atoms, an alkenyl group having 2 to 20 carbon atoms or a cycloalkyl group having 3 to 20 ring-forming carbon atoms).

The same groups as in a case of $R^1$ and $R^2$ can be shown as the examples of the alkyl group having 1 to 20 carbon atoms, the alkenyl group having 2 to 20 carbon atoms and the cycloalkyl group having 3 to 20 ring-forming carbon atoms each represented by $R^3$. Among them, $R^3$ is preferably an alkyl group having 1 to 20 carbon atoms, from the viewpoint of a usefulness thereof as a raw material for medical products and agricultural chemicals, more preferably an alkyl group having 1 to 5 carbon atoms and further preferably methyl or ethyl.

The specific examples of the aliphatic alcohol used in the present invention include methanol, ethanol, n-propyl alcohol, isopropyl alcohol, isobutyl alcohol, n-butyl alcohol and the like, and it is suitably selected according to the kind of the targeted product. From the viewpoint of a usefulness thereof as a raw material for medical products and agricultural chemicals, methanol or ethanol is preferred.

A use amount of the aliphatic alcohol is preferably 1 to 50 times mole, more preferably 2 to 30 times mole and further preferably 5 to 30 times mole based on the α-hydroxycarboxylic amide.

Gas Phase Reaction:

The present invention is a gas phase reaction in which a solid catalyst is used in a fixed bed or a fluid bed. In the present invention, the higher conversion rate as compared with in a case of a liquid phase reaction is obtained, and this is estimated to be attributable to that in the present invention which is a gas phase reaction, equilibrium between the raw materials and the product inclines to a product side to a large extent.

In the present invention, the "gas phase reaction" means reaction carried out principally in a gas phase, in which a proportion of a liquid phase is 10% by mass or less, preferably 5% by mass or less, more preferably 2% by mass or less and further preferably substantially 0% by mass based on a total amount of the raw materials. The α-hydroxycarboxylic amide and the aliphatic alcohol which are the raw materials may be vaporized before supplied to a reactor or may be vaporized in the reactor. Also, the α-hydroxycarboxylic amide and the aliphatic alcohol each may be supplied separately to the reactor or may be supplied to the reactor after mixed.

If the reaction is carried out in an atmosphere of an inert gas such as a nitrogen gas, the raw materials are reduced in a partial pressure by the presence of the inert gas and readily vaporized, and therefore it is preferred.

When the α-hydroxycarboxylic amide and the aliphatic alcohol which are the raw materials are vaporized in the reactor, the above raw materials may be supplied to the reactor together with a solvent. The above solvent includes, for example, ether base solvent such as tetrahydrofuran and the like; amide base solvent such as N-methylpyrrolidone and the like; and ester base solvent such as methyl lactate and the like. In the present invention, the reaction proceeds efficiently without using the above solvents.

The reaction temperature is set so that the α-hydroxycarboxylic amide and the aliphatic alcohol which are the raw materials are vaporized in the reaction system. The set temperature is varied according to various conditions such as the kinds of the raw materials, a mole ratio of the α-hydroxycarboxylic amide and the aliphatic alcohol used, the presence or absence of the inert gas, the presence or absence of the solvent, the reaction pressure and the like. Usually, it is preferably 150 to 270° C., more preferably 170 to 250° C., further preferably 180 to 240° C. and particularly preferably 180 to 210° C.

When the α-hydroxycarboxylic amide is, for example, α-hydroxyisobutyroamide, the satisfactory reaction rate is obtained by setting the reaction temperature to 150° C. or higher, but in order to sufficiently vaporize α-hydroxyisobutyroamide at an atmospheric pressure, it is efficient to carry out the reaction at 180° C. or higher. Further, setting the reaction pressure to 240° C. or lower makes it possible to reduce decomposition of α-hydroxyisobutyroamide to acetone and the amounts of by-products such as α-alkoxyisobutyric esters and olefin derivatives which are dehydration products.

The reaction is carried out usually under an atmospheric pressure or a reduced pressure. Also, the reaction may be carried out under an applied pressure if it is a condition on which the α-hydroxycarboxylic amide and the aliphatic alcohol of the raw materials are vaporized.

The α-hydroxycarboxylic amide has a high boiling point, for example, α-hydroxyisobutyroamide has a boiling point of 260° C., and therefore it is easier to vaporize the raw materials under an atmospheric pressure or a reduced pressure. Accordingly, the reaction pressure is preferably 1 to 300 kPa, more preferably 10 to 150 kPa, further preferably 30 to 120 kPa and particularly preferably 30 kPa to an atmospheric pressure.

A supplying rate of the raw materials is, from the viewpoint of continuing the high conversion rate for long time, preferably 0.01 to 5 $hr^{-1}$, more preferably 0.02 to 2 $hr^{-1}$, further preferably 0.03 to 1 $hr^{-1}$ and particularly preferably 0.05 to 0.5 $hr^{-1}$ in terms of a weight of the α-hydroxycarboxylic amide per a unit weight of the catalyst, that is, a weight hourly space velocity (WHSV) based on the α-hydroxycarboxylic amide.

Similarly, the weight hourly space velocity (WHSV) based on the aliphatic alcohol can be calculated from the relation of the use amounts of the α-hydroxycarboxylic amide and the aliphatic alcohol, and it is preferably approximately 0.01 to 100 $hr^{-1}$, more preferably 0.04 to 40 $hr^{-1}$ and further preferably 0.10 to 2 $hr^{-1}$.

A method for separating the α-hydroxycarboxylic ester from the products obtained by the method described above shall not specifically be restricted. For example, ammonia is removed together with the aliphatic alcohol by an ordinary distillation operation to obtain the α-hydroxycarboxylic ester and the unreacted aliphatic alcohol and α-hydroxycarboxylic amide from a column bottom of the distillation column, and the α-hydroxycarboxylic ester can be isolated by an ordinary distillation operation.

EXAMPLES

The present invention shall specifically be explained below with reference to examples, but the present invention shall by no means be restricted by the examples shown below.

The reaction results in the respective examples were determined by gas chromatographic analysis according to the following conditions.

Analytical conditions of gas chromatography:
Equipment: 6850A (manufactured by Agilent Technologies Inc.)
Column used: DB-WAX (manufactured by Agilent Technologies Inc.)
Analytical conditions: injection inlet temperature 200° C., detector temperature 250° C.
Column temperature: after maintained at 50° C. for 3 minutes, the temperature was elevated up to 250° C. at 15° C./minute
Detector: thermal conductivity detector (TCD)

Example 1

Preparation of Catalyst

Zirconium hydroxide "XZO 1501/03" manufactured by MEL Chemicals Inc. was molded by compression, and the molded matter was crushed and controlled to 10 to 20 mesh. This was dried at 150° C. for 3 hours, then burned at 400° C. for 3 hours and controlled again to 10 to 20 mesh to prepare a zirconium dioxide catalyst.

Pre-Treatment:
A SUS316-made reaction tube having an inner diameter of 18 mmφ was charged with 14 g of the zirconium dioxide catalyst prepared above. The reaction tube was heated in an electric furnace while allowing nitrogen to flow at 40 ml/minute, and the zirconium dioxide catalyst charged was heated at 250° C. for 3 hours and subjected to pre-treatment.

Reaction:
Nitrogen was stopped being supplied after controlling a temperature of the catalyst layer to 220° C., and a raw material liquid prepared by mixing α-hydroxyisobutyroamide and methanol in a proportion of 30 parts by mass to 70 parts by mass was allowed to flow through the reaction tube at a flow rate of 4.67 g/hour (WHSV based on α-hydroxyisobutyroamide=0.1 $hr^{-1}$). The reaction of almost 100% by mass of the raw materials proceeded in a gas phase in the reaction tube.

When the reaction reached a steady state after about 24 hours passed, the products were sampled in an ice trap and analyzed by means of a gas chromatography to find that a conversion rate of α-hydroxyisobutyroamide was 95% and that a selectivity of methyl α-hydroxyisobutyrate was 88%. The reaction was continued to find that a conversion rate of α-hydroxyisobutyroamide could be maintained at 90% or more for 992 hours since starting the reaction. The conversion rate and the selectivity after about 24 hours passed and time for which a conversion rate of 90% or more could be maintained when the reaction was continued (hereinafter referred to merely as the reaction results) are shown in Table 1.

Examples 2 to 5

Preparation of Catalysts

Catalysts shown in Table 1 each manufactured by MEL Chemicals Inc. were molded by compression, and the molded matters were crushed and controlled to 10 to 20 mesh. "XZO 1501/10", "XZO 1501/07" and "XZO 882/03" (Examples 2, 3 and 5) which are zirconium dioxide catalysts subjected to burning were dried at 150° C. for 12 hours or longer, and a non-burned catalyst "XZO 632/03" (Example 4) was dried, as was the case with Example 1, at 150° C. for 3 hours, then burned at 400° C. for 3 hours and controlled again to 10 to 20 mesh.

The catalysts described above were offered as samples by MEL Chemicals Inc.; "XZO 1501/10" is zirconium dioxide; "XZO 1501/07" is zirconium dioxide obtained by burning "XZO 1501/03"; "XZO 882/03" is zirconium dioxide obtained by burning zirconium hydroxide; "XZO 632/03" is zirconium dioxide obtained by burning zirconium hydroxide which is different from a "XZO 1501" series and a "XZO 632" series; and the above catalysts are different respectively in a BET specific surface area, a particle diameter, trace amount impurities comprising principally metals and the like.

Pre-Treatment and Reaction:

The pre-treatment and the reaction were carried out in the same manners as in Example 1, except that various zirconium dioxide catalysts prepared above were used. The reaction results are shown in Table 1.

Example 6

Preparation of Catalyst

Zirconium hydroxide "NN zirconium hydroxide" manufactured by Daiichi Kigennso Kagaku Kogyo Co., Ltd. was molded by compression, and the molded matter was crushed and controlled to 10 to 20 mesh. This was dried, as was the case with Example 1, at 150° C. for 3 hours, then burned at 400° C. for 3 hours and controlled again to 10 to 20 mesh.

Pre-Treatment and Reaction:

The pre-treatment and the reaction were carried out in the same manners as in Example 1, except that the zirconium dioxide catalyst prepared above was used. The reaction results are shown in Table 1.

Example 7

Preparation of Catalyst

Zirconium hydroxide "RSC-HP" manufactured by Daiichi Kigennso Kagaku Kogyo Co., Ltd. was crushed, controlled to 10 to 20 mesh and dried at 150° C. for 3 hours.

Pre-Treatment and Reaction:

The pre-treatment and the reaction were carried out in the same manners as in Example 1, except that the zirconium dioxide catalyst prepared above was used. The reaction results are shown in Table 1.

TABLE 1

| | | Reaction temperture (° C.) | Reaction pressure (kPa) | Catalyst | WHSV based on α-hydroxy-carboxylic amide ($hr^{-1}$) | Reaction results After 24 hours Conversion rate (%) | Selectivity (%) | Time for which conversion rate of 90% or more could be maintained (hr) |
|---|---|---|---|---|---|---|---|---|
| Example | 1 | 220 | 101.3 | XZO 1501/03 | 0.1 | 95 | 88 | 992 |
| | 2 | 220 | 101.3 | XZO 1501/10 | 0.1 | 95 | 82 | 624 |
| | 3 | 220 | 101.3 | XZO 1501/07 | 0.1 | 95 | 88 | 315 |
| | 4 | 220 | 101.3 | XZO 632/03 | 0.1 | 95 | 90 | 288 |
| | 5 | 220 | 101.3 | XZO 882/03 | 0.1 | 91 | 62 | 30 |
| | 6 | 220 | 101.3 | NN zirconium hydroxide | 0.1 | 95 | 86 | 980 |
| | 7 | 220 | 101.3 | RSC-HP | 0.1 | 62 | 82 | 0 |

Reference Example 1

The pre-treatment and the reaction were carried out on the same conditions, except that in Example 3, a temperature (reaction temperature) of the catalyst layer was changed to 190° C.

A conversion rate of α-hydroxyisobutyroamide after about 24 hours passed was 37%, and a selectivity of methyl α-hydroxyisobutyrate was 94%. Since a vapor pressure of the raw materials was not sufficiently secured on the above reaction conditions, a part of the raw material gases was liquefied in the reaction system, and this was considered to lead to a reduction of the conversion rate. The reaction results after about 24 hours passed are shown in Table 2.

Example 8

The pre-treatment and the reaction were carried out on the same conditions, except that in Reference Example 1, nitrogen was introduced at 54 ml/minute together with the raw materials so that the raw materials were sufficiently vaporized. The reaction results after about 24 hours passed are shown in Table 2. It can be found from the results obtained in Reference Example 1 and Example 8 that it is important to set a presence proportion of the liquid phase to substantially 0% by mass in order to obtain the high conversion rate.

Examples 9 to 12

The pre-treatment and the reaction were carried out on the same conditions, except that in Example 3, a temperature (reaction temperature) of the catalyst layer was changed to 200° C., 230° C., 240° C. and 250° C. respectively. The reaction results after about 24 hours passed are shown in Table 2.

TABLE 2

| | | Reaction temperature (° C.) | Reaction pressure (kPa) | Catalyst | WHSV based on α-hydroxy-carboxylic amide (hr⁻¹) | Reaction results After 24 hours | |
|---|---|---|---|---|---|---|---|
| | | | | | | Conversion rate (%) | Selectivity (%) |
| Reference Example | 1 | 190 | 101.3 | XZO 1501/07 | 0.1 | 37 | 94 |
| Example | 8 | 190 | 101.3 | XZO 1501/07 | 0.1 | 95 | 95 |
| | 9 | 200 | 101.3 | XZO 1501/07 | 0.1 | 95 | 93 |
| | 3 | 220 | 101.3 | XZO 1501/07 | 0.1 | 95 | 88 |
| | 10 | 230 | 101.3 | XZO 1501/07 | 0.1 | 95 | 86 |
| | 11 | 240 | 101.3 | XZO 1501/07 | 0.1 | 95 | 84 |
| | 12 | 250 | 101.3 | XZO 1501/07 | 0.1 | 95 | 76 |

Example 13

The pre-treatment and the reaction were carried out on the same conditions, except that in Example 1, a use amount of the zirconium dioxide catalyst was changed to 7 g (WHSV based on α-hydroxyisobutyroamide=0.2 hr⁻¹). The reaction results are shown in Table 3.

Comparative Example 1

Preparation of Catalyst

Lanthanum nitrate (La(NO$_2$)$_2$.6H$_2$O) 56.3 g was dissolved in 400 g of purified water, and then the solution was heated to 50° C. An aqueous solution prepared by dissolving 40.6 g of sodium hydrogenphosphate (Na$_2$HPO$_4$) in 400 g of purified water was added to the above solution, and a white precipitate was formed. The above white precipitate was separated by filtration and washed with 600 g of purified water, and then after dried at 120° C. for 3 hours, it was burned at 400° C. for 6 hours under aerial atmosphere, whereby a lanthanum phosphate catalyst (LaPO$_4$) was obtained. This was crushed and controlled to a size of 10 to 20 mesh.

Pre-Treatment and Reaction:

The catalyst 7 g prepared above was used to carry out the pre-treatment and the reaction on the same conditions as in Example 13. The reaction results are shown in Table 3.

Comparative Example 2

The pre-treatment and the reaction were carried out on the same conditions, except that in Comparative Example 1, a temperature (reaction temperature) of the catalyst layer was changed to 250° C. The reaction results are shown in Table 3.

Comparative Example 3

Preparation of Catalyst

NaH$_2$PO$_4$ 4 g was dissolved in 20 g of water, and 6 g of silica gel "CARiACTQ-50" (manufactured by Fuji Silysia Chemical Ltd.) was added thereto and stirred at 50° C. for 30 minutes. Then, water was removed by an evaporator, and the residue was dried at 120° C. for 3 hours and then burned at 500° C. for 6 hours under aerial atmosphere to obtain a catalyst in which NaH$_2$PO$_4$ was carried on a silica carrier.

Pre-Treatment and Reaction:

The pre-treatment and the reaction were carried out on the same conditions as in Example 13, except that the catalyst 7 g prepared above was used. The reaction results are shown in Table 3.

Comparative Example 4

The pre-treatment and the reaction were carried out on the same conditions, except that in Comparative Example 3, a temperature (reaction temperature) of the catalyst layer was changed to 250° C. The reaction results are shown in Table 3.

Comparative Example 5

Preparation of Catalyst

MgSO$_4$ (manufactured by Wako Pure Chemical Industries, Ltd.) was molded by compression, and then the molded matter was burned at 500° C. for 6 hours. This was crushed and controlled to a size of 10 to 20 mesh.

Pre-Treatment and Reaction:

The pre-treatment and the reaction were carried out on the same conditions as in Example 13, except that the catalyst 7 g prepared above was used. The reaction results are shown in Table 3.

Comparative Example 6

The pre-treatment and the reaction were carried out in the same manner, except that in Example 1, a silica titania catalyst "HTG-30705" (manufactured by Fuji Silysia Chemical Ltd.) 14 g was used in place of the zirconium dioxide catalyst 14 g. The reaction results are shown in Table 3.

Comparative Example 7

The pre-treatment and the reaction were carried out in the same manner, except that in Example 1, a titania catalyst "CS-300S-24" (manufactured by Sakai Chemical Industry Co., Ltd.) 14 g was used in place of the zirconium dioxide catalyst 14 g. The reaction results are shown in Table 3.

Comparative Example 8

The pre-treatment and the reaction were carried out on the same conditions, except that in Example 13, a zeolite catalyst "ZSM-5 K⁺ type" (manufactured by N.E. Chemcat Corporation) 7 g was used in place of the zirconium dioxide catalyst 7 g and that a temperature (reaction temperature) of the catalyst layer was changed to 250° C. The reaction results are shown in Table 3.

Comparative Example 9

The pre-treatment and the reaction were carried out on the same conditions, except that in Example 13, a γ-alumina catalyst "KHS-24" (manufactured by Sumitomo Chemical Co., Ltd.) 7 g was used in place of the zirconium dioxide catalyst 7 g. The reaction results are shown in Table 3.

Comparative Example 10

The pre-treatment and the reaction were carried out on the same conditions, except that in Example 13, a tin oxide catalyst (catalyst obtained by subjecting "MM-002" manufactured by Mitsui Mining & Smelting Co., Ltd. to compression molding and controlling a size thereof to 10 to 20 mesh) 7 g was used in place of the zirconium dioxide catalyst 7 g. The reaction results are shown in Table 3.

Comparative Example 11

The pre-treatment and the reaction were carried out on the same conditions, except that in Example 13, a magnesium oxide catalyst (catalyst obtained by subjecting "UCM150" manufactured by Ube Material Industries, Ltd. to compression molding and controlling a size thereof to 10 to 20 mesh) 7 g was used in place of the zirconium dioxide catalyst 7 g. The reaction results are shown in Table 3.

Comparative Example 12

The pre-treatment and the reaction were carried out on the same conditions, except that in Example 13, a silica magnesia catalyst "Mizukalife P-1G" (manufactured by Mizusawa Industrial Chemicals, Ltd.) 7 g was used in place of the zirconium dioxide catalyst 7 g. The reaction results are shown in Table 3.

Comparative Example 13

The pre-treatment and the reaction were carried out on the same conditions, except that in Example 13, an antimony trioxide catalyst (catalyst obtained by subjecting antimony trioxide manufactured by Soekawa Chemical Co., Ltd. to compression molding and controlling a size thereof to 10 to 20 mesh) 7 g was used in place of the zirconium dioxide catalyst 7 g. The reaction results are shown in Table 3.

Comparative Example 14

Preparation of Catalyst

A zeolite catalyst "MCM41" (manufactured by N.E. Chemcat Corporation) was kneaded with a binder "Ben-gel 11" (manufactured by Nihon Yuki Nendo Co., Ltd.) in a mass ratio of 9:1. A clayey matter obtained by adding water to the above kneaded matter was dried at 150° C. for 3 hours and then burned at 400° C. for 3 hours, and the burned matter was crushed and controlled to 10 to 20 mesh.
Pre-Treatment and Reaction:
The pre-treatment and the reaction were carried out on the same conditions as in Example 13, except that the catalyst 7 g prepared above was used. The reaction results are shown in Table 3.

Comparative Example 15

The pre-treatment and the reaction were carried out on the same conditions, except that in Example 13, a hydroxyapatite catalyst (catalyst obtained by subjecting hydroxyapatite manufactured by Wako Pure Chemical Industries, Ltd. to compression molding and controlling a size thereof to 10 to 20 mesh) 7 g was used in place of the zirconium dioxide catalyst 7 g. The reaction results are shown in Table 3.

Comparative Example 16

The pre-treatment and the reaction were carried out on the same conditions, except that in Example 13, a lead oxide catalyst (catalyst obtained by subjecting lead oxide manufactured by Wako Pure Chemical Industries, Ltd. to compression molding and controlling a size thereof to 10 to 20 mesh) 7 g was used in place of the zirconium dioxide catalyst 7 g. The reaction results are shown in Table 3.

Comparative Example 17

Preparation of Catalyst

A zeolite catalyst "HSZ 310NAD" (manufactured by Tosoh Corporation) was kneaded with the binder "Ben-gel 11" (manufactured by Nihon Yuki Nendo Co., Ltd.) in a mass ratio of 9:1. A clayey matter obtained by adding water to the above kneaded matter was dried at 150° C. for 3 hours and then burned at 400° C. for 3 hours, and the burned matter was crushed and controlled to 10 to 20 mesh.
Pre-Treatment and Reaction:
The pre-treatment and the reaction were carried out on the same conditions as in Example 13, except that the catalyst 7 g prepared above was used. The reaction results are shown in Table 3.

Comparative Example 18

Preparation of Catalyst $NH_4VO_3$ 6.43 g was added to 100 g of water, and 10.40 g of oxalic acid dihydrate was added thereto little by little to dissolve $NH_4VO_3$. Silica gel "CARiACTQ-50" (manufactured by Fuji Silysia Chemical Ltd.) 20 g was added thereto and stirred at 50° C. for 2 hours. Then, water was removed by an evaporator, and the residue was dried at 150° C. for 3 hours and then burned at 400° C. for 24 hours under aerial atmosphere to obtain a catalyst.
Pre-Treatment and Reaction:
The pre-treatment and the reaction were carried out on the same conditions as in Example 13, except that the catalyst 7 g prepared above was used. The reaction results are shown in Table 3.

Comparative Example 19

Preparation of Catalyst

Bismuth hydroxide (manufactured by Soekawa Chemical Co., Ltd.) was molded by compression and burned at 400° C. for 3 hours under aerial atmosphere, and then the catalyst was crushed and controlled to a size of 10 to 20 mesh to obtain a bismuth oxide catalyst.
Pre-Treatment and Reaction:
The pre-treatment and the reaction were carried out on the same conditions as in Example 13, except that the catalyst 7 g prepared above was used. The reaction results are shown in Table 3.

Comparative Example 20

Preparation of Catalyst

Calcium hydroxide (manufactured by Wako Pure Chemical Industries, Ltd.) was molded by compression and burned at 500° C. for 3 hours under aerial atmosphere, and then the catalyst was crushed and controlled to a size of 10 to 20 mesh to obtain a calcium oxide catalyst.

Pre-Treatment and Reaction:

The pre-treatment and the reaction were carried out on the same conditions as in Example 13, except that the catalyst 7 g prepared above was used. The reaction results are shown in Table 3.

Comparative Example 21

Preparation of Catalyst

A zeolite catalyst "HSZ 610NAA" (manufactured by Tosoh Corporation) was kneaded with the binder "Ben-gel 11" (manufactured by Nihon Yuki Nendo Co., Ltd.) in a mass ratio of 9:1. A clayey matter obtained by adding water to the above kneaded matter was dried at 150° C. for 3 hours and then burned at 400° C. for 3 hours, and the burned matter was crushed and controlled to 10 to 20 mesh.

Pre-Treatment and Reaction:

The pre-treatment and the reaction were carried out on the same conditions as in Example 13, except that the catalyst 7 g prepared above was used. The reaction results are shown in Table 3.

Comparative Example 22

Preparation of Catalyst

A zeolite catalyst "Mizukasieves 13X-15P Na$^+$ type" (manufactured by Mizusawa Industrial Chemicals, Ltd.) was kneaded with the binder "Ben-gel 11" (manufactured by Nihon Yuki Nendo Co., Ltd.) in a mass ratio of 9:1. A clayey matter obtained by adding water to the above kneaded matter was dried at 150° C. for 3 hours and then burned at 400° C. for 3 hours, and the burned matter was crushed and controlled to 10 to 20 mesh.

Pre-Treatment and Reaction:

The pre-treatment and the reaction were carried out on the same conditions as in Example 13, except that the catalyst 7 g prepared above was used. The reaction results are shown in Table 3.

Comparative Example 23

Preparation of Catalyst

Zinc hydroxide (manufactured by Soekawa Chemical Co., Ltd.) was molded by compression and burned at 500° C. for 3 hours under aerial atmosphere, and then the catalyst was crushed and controlled to a size of 10 to 20 mesh to obtain a zinc oxide catalyst.

Pre-Treatment and Reaction:

The pre-treatment and the reaction were carried out on the same conditions as in Example 13, except that the catalyst 7 g prepared above was used. The reaction results are shown in Table 3.

Comparative Example 24

Preparation of Catalyst

An aqueous solution prepared by dissolving 0.33 mol of manganese sulfate monohydrate in 215 ml of water under stirring at 75° C. and then mixing the solution with 0.958 mol of conc. sulfuric acid was added quickly to an aqueous solution prepared by dissolving 0.398 mol of potassium permanganate in 220 of water. The solution was continuously stirred at 70° C. for 2 hours and further stirred at 90° C. for 4 hours to be ripened, and then a mixed solution prepared by suspending 0.007 mol of bismuth (III) oxide in 440 ml of water was quickly added thereto After stirred at room temperature for 30 minutes, the resulting precipitate was filtrated and washed four times with 2000 ml of water to obtain a precipitate cake. The cake thus obtained was dried at 110° C. for a night, crushed and controlled to a size of 10 to 20 mesh to obtain a manganese dioxide catalyst.

Pre-Treatment and Reaction:

The catalyst 7 g prepared above was used to carry out the pre-treatment and the reaction on the same conditions as in Example 13. The reaction results are shown in Table 3.

TABLE 3

| | | Reaction temperature (° C.) | Reaction pressure (kPa) | Catalyst | WHSV based on α-hydroxy-carboxylic amide (hr$^{-1}$) | Reaction results | | Time for which conversion rate of 90% or more could be maintained (hr) |
| | | | | | | After 24 hours | | |
| | | | | | | Conversion rate (%) | Selectivity (%) | |
|---|---|---|---|---|---|---|---|---|
| Example | 1 | 220 | 101.3 | XZO 1501/03 | 0.1 | 95 | 88 | 992 |
| | 13 | 220 | 101.3 | XZO 1501/03 | 0.2 | 95 | 89 | 333 |
| Comparative | 1 | 220 | 101.3 | LaPO$_4$ | 0.2 | 22 | 25 | 0 |
| Example | 2 | 250 | 101.3 | LaPO$_4$ | 0.2 | 57 | 21 | 0 |
| | 3 | 220 | 101.3 | NaH$_2$PO$_4$—SiO$_2$ | 0.2 | 21 | 7 | 0 |
| | 4 | 250 | 101.3 | NaH$_2$PO$_4$—SiO$_2$ | 0.2 | 28 | 11 | 0 |
| | 5 | 220 | 101.3 | MgSO$_4$ | 0.2 | 12 | 2 | 0 |
| | 6 | 220 | 101.3 | TiO—SiO$_2$ | 0.1 | 90 | 53 | 23 |
| | 7 | 220 | 101.3 | TiO$_2$ | 0.1 | 43 | 30 | 0 |
| | 8 | 250 | 101.3 | ZSM-5 | 0.2 | 19 | 54 | 0 |
| | 9 | 220 | 101.3 | γ-alumina | 0.2 | 17 | 48 | 0 |
| | 10 | 220 | 101.3 | SnO$_2$ | 0.2 | 36 | 19 | 0 |
| | 11 | 220 | 101.3 | MgO | 0.2 | 30 | 18 | 0 |
| | 12 | 220 | 101.3 | SiO$_2$—MgO | 0.2 | 28 | 18 | 0 |
| | 13 | 220 | 101.3 | Sb$_2$O$_3$ | 0.2 | 20 | 14 | 0 |
| | 14 | 220 | 101.3 | MCM41 | 0.2 | 32 | 14 | 0 |
| | 15 | 220 | 101.3 | Ca$_{10}$(PO$_4$)$_6$(OH)$_2$ | 0.2 | 20 | 12 | 0 |

TABLE 3-continued

| | Reaction temperature (° C.) | Reaction pressure (kPa) | Catalyst | WHSV based on α-hydroxy-carboxylic amide (hr$^{-1}$) | Reaction results | | Time for which conversion rate of 90% or more could be maintained (hr) |
|---|---|---|---|---|---|---|---|
| | | | | | After 24 hours | | |
| | | | | | Conversion rate (%) | Selectivity (%) | |
| 16 | 220 | 101.3 | PbO | 0.2 | 22 | 12 | 0 |
| 17 | 220 | 101.3 | HSZ 310NAD | 0.2 | 16 | 12 | 0 |
| 18 | 220 | 101.3 | $V_2O_5$—$SiO_2$ | 0.2 | 19 | 8 | 0 |
| 19 | 220 | 101.3 | $Bi_2O_3$ | 0.2 | 55 | 6 | 0 |
| 20 | 220 | 101.3 | CaO | 0.2 | 76 | 4 | 0 |
| 21 | 220 | 101.3 | HSZ 610NAA | 0.2 | 8 | 4 | 0 |
| 22 | 220 | 101.3 | Mizukasieves 13X-15P Na$^+$ type | 0.2 | 7 | 2 | 0 |
| 23 | 220 | 101.3 | ZnO | 0.2 | 18 | 1 | 0 |
| 24 | 220 | 101.3 | $MnO_2$ | 0.2 | 24 | 1 | 0 |

Comparative Example 25

Liquid Phase Reaction (Method in which a Titanium Base Catalyst was used and in which Ammonia was not Removed to an Outside of the System)

Preparation of Catalyst:

α-Hydroxyisobutyroamide 65.3 g was dissolved in 1000 g of isopropanol, and a solution prepared by dissolving 30 g of titanium tetraisopropoxide in 1000 g of isopropanol was added thereto. Isopropanol was removed from the above solution by means of a rotary evaporator, and the solution was concentrated up to 840 g and left standing at room temperature for 24 hours. After 24 hours passed, a white precipitate deposited was separated by filtering, washed with heptane and then dried under vacuum to obtain a complex in which α-hydroxyisobutyroamide was coordinated with titanium (hereinafter referred to as Ti(HBD)$_4$).

Reaction:

A SUS316-made autoclave having a capacity of 20 ml was charged with 5.4 g of α-hydroxyisobutyroamide, 12.6 g of methanol and 0.1 g of Ti(HBD)$_4$ as a catalyst, and they were reacted at 200° C. for 3 hours while stirring the content by means of a magnetic stirrer.

The content was cooled and analyzed by a gas chromatography to find that a concentration of α-hydroxyisobutyroamide was 21.8% by mass; a concentration of N-methyl-α-hydroxyisobutyroamide was 0.3% by mass; a concentration of methyl α-hydroxyisobutyrate was 8.8% by mass; a concentration of methanol was 64.8% by mass; a concentration of ammonia was 1.2% by mass; a conversion rate of α-hydroxyisobutyroamide in the above reaction was 27%; a selectivity of methyl α-hydroxyisobutyrate was 94%; and a selectivity of N-methyl-α-hydroxyisobutyroamide was 3%.

Reference Example 2

Liquid Phase Reaction (Method in which a Titanium Base Catalyst was used and in which Ammonia was Removed to an Outside of the System)

A SUS316-made autoclave having a capacity of 300 ml equipped with a jacket type reflux condenser and a stirrer was charged with 30.0 g of α-hydroxyisobutyroamide, 100 g of methanol and 6.00 g of Ti(HBD)$_4$ prepared in Comparative Example 25. The autoclave was maintained at a temperature of 190° C. and a pressure of 3.0 MPa while stirring to carry out reaction for one hour while supplying a nitrogen gas at a flow amount of 87 L/hour and methanol at a flow amount of 158 g/hour. In this case, oil of 185° C. was circulated through the jacket of the reflux condenser to heat it, and methanol was taken out to an outside of the system together with ammonia at a rate of 158 g/hour so that internal refluxing was not brought about.

After finishing the reaction, the reaction liquid was cooled and analyzed by a gas chromatography to find that a conversion rate of α-hydroxyisobutyroamide was 93%; a selectivity of methyl α-hydroxyisobutyrate was 97%; and a selectivity of N-methyl-α-hydroxyisobutyroamide was 3%.

Thus, it has been found that in the method of Comparative Example 25, the conversion rate can be improved by carrying out the reaction while removing by-produced ammonia to an outside of the system.

Example 14

The pre-treatment and the reaction were carried out on the same conditions, except that in Example 1, a use amount of the catalyst was set to 7 g and that a flow rate of the raw material liquid was changed to 7.00 g/hour (WHSV based on α-hydroxyisobutyroamide=0.3 hr$^{-1}$). The reaction results are shown in Table 4.

Example 15

Preparation of Catalyst: Impregnation Method

Zirconium hydroxide "XZO 1501/03" (manufactured by MEL Chemicals Inc.) was molded by compression, and the molded matter was crushed and controlled to 10 to 20 mesh. This zirconium hydroxide 14.6 g (78% by mass in terms of $ZrO_2$) was added to an aqueous solution prepared by dissolving in advance 0.377 g of $ZrO(NO_3)_2 \cdot 2H_2O$ (added element source) in 20 g of water, and the mixture was stirred at 50° C. for 30 minutes. Then, water was removed by means of an evaporator, and the residue was dried at 150° C. for 3 hours, then burned at 400° C. for 3 hours and controlled again to 10 to 20 mesh to prepare a zirconium dioxide catalyst containing a zirconium element (Zr).

Pre-Treatment and Reaction:

The zirconium dioxide catalyst 7 g prepared above was used to carry out pre-treatment and reaction on the same conditions as in Example 14. The reaction results are shown in Table 4.

Example 16

Preparation of Catalyst: Impregnation Method

A zirconium dioxide catalyst (mole ratio in the catalyst Zr:Y=98.5:1.5) was prepared in the same manner as in Example 15, except that the added element source was changed to 0.487 g of $Y(CH_3COO)_3 \cdot 4H_2O$ to add yttrium (Y) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 17

Preparation of Catalyst: Impregnation Method

A zirconium dioxide catalyst (mole ratio in the catalyst Zr:La=98.5:1.5) was prepared in the same manner as in Example 15, except that the added element source was changed to 0.611 g of $La(NO_3)_3 \cdot 6H_2O$ to add lanthanum (La) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 18

Preparation of Catalyst: Impregnation Method

A zirconium dioxide catalyst (mole ratio in the catalyst Zr:Co=98.5:1.5) was prepared in the same manner as in Example 15, except that the added element source was changed to 0.410 g of $Co(NO_3)_2 \cdot 6H_2O$ to add cobalt (Co) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 19

Preparation of Catalyst: Impregnation Method

A zirconium dioxide catalyst (mole ratio in the catalyst Zr:Mn=98.5:1.5) was prepared in the same manner as in Example 15, except that the added element source was changed to 0.346 g of $Mn(CH_3COO)_2 \cdot 4H_2O$ to add manganese (Mn) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 20

Preparation of Catalyst: Impregnation Method

A zirconium dioxide catalyst (mole ratio in the catalyst Zr:Ni=98.5:1.5) was prepared in the same manner as in Example 15, except that the added element source was changed to 0.351 g of $Ni(CH_3COO)_2 \cdot 4H_2O$ to add nickel (Ni) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 21

Preparation of Catalyst: Impregnation Method

A zirconium dioxide catalyst (mole ratio in the catalyst Zr:Yb=98.5:1.5) was prepared in the same manner as in Example 15, except that the added element source was changed to 0.608 g of $Yb(NO_3)_3 \cdot 4H_2O$ to add ytterbium (Yb) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 22

Preparation of Catalyst: Impregnation Method

A zirconium dioxide catalyst (mole ratio in the catalyst Zr:Al=98.5:1.5) was prepared in the same manner as in Example 15, except that the added element source was changed to 0.529 g of $Al(NO_3)_3 \cdot 9H_2O$ to add aluminum (Al) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 23

Preparation of Catalyst: Impregnation Method

A zirconium dioxide catalyst (mole ratio in the catalyst Zr:B=98.5:1.5) was prepared in the same manner as in Example 15, except that the added element source was changed to 0.087 g of $H_3BO_3$ to add boron (B) to the catalyst.
Pre-Treatment and Reaction:

The zirconium dioxide catalyst 7 g prepared above was used to carry out the pre-treatment and the reaction on the same conditions as in Example 14. The reaction results are shown in Table 4.

Example 24

Preparation of Catalyst: Impregnation Method

A zirconium dioxide catalyst (mole ratio in the catalyst Zr:Cu=98.5:1.5) was prepared in the same manner as in Example 15, except that the added element source was changed to 0.281 g of $Cu(CH_3COO)_2 \cdot H_2O$ to add copper (Cu) to the catalyst.
Pre-Treatment and Reaction:
The zirconium dioxide catalyst 7 g prepared above was used to carry out the pre-treatment and the reaction on the same conditions as in Example 14. The reaction results are shown in Table 4.

Example 25

Preparation of Catalyst: Impregnation Method

A zirconium dioxide catalyst (mole ratio in the catalyst Zr:Ce=98.5:1.5) was prepared in the same manner as in Example 15, except that the added element source was changed to 0.612 g of $Ce(NO_3)_3 \cdot 6H_2O$ to add cerium (Ce) to the catalyst.
Pre-Treatment and Reaction:
The zirconium dioxide catalyst 7 g prepared above was used to carry out the pre-treatment and the reaction on the same conditions as in Example 14. The reaction results are shown in Table 4.

Example 26

Preparation of Catalyst: Impregnation Method

Zirconium hydroxide "XZO 1501/03" manufactured by MEL Chemicals Inc. was molded by compression, and the molded matter was crushed and controlled to 10 to 20 mesh. This zirconium hydroxide 14.6 g (78% by mass in terms of $ZrO_2$) was added to an aqueous solution prepared by dissolving in advance 0.367 g of $Bi(OH)_3$ (added element source) in 20 g of water by 1 mL of 1N nitric acid, and the mixture was stirred at 50° C. for 30 minutes. Then, water was removed by means of an evaporator, and the residue was dried at 150° C. for 3 hours, then burned at 400° C. for 3 hours and controlled again to 10 to 20 mesh to prepare a zirconium dioxide catalyst containing a bismuth element (Bi).
Pre-Treatment and Reaction:
The zirconium dioxide catalyst (mole ratio in the catalyst Zr:Bi=98.5:1.5) 7 g prepared above was used to carry out the pre-treatment and the reaction on the same conditions as in Example 14. The reaction results are shown in Table 4.

Example 27

Preparation of Catalyst: Impregnation Method

Zirconium hydroxide "XZO 1501/03" manufactured by MEL Chemicals Inc. was molded by compression, and the molded matter was crushed and controlled to 10 to 20 mesh. This zirconium hydroxide 14.6 g (78% by mass in terms of $ZrO_2$) was added to a solution prepared by dissolving in advance 0.401 g of $Ti(OCH(CH_3)_2)_4$ (added element source) in 20 ml of isopropanol, and the mixture was stirred at 50° C. for 30 minutes. Then, 1 ml of water was added thereto, and isopropanol was removed by means of an evaporator. The residue was dried at 150° C. for 3 hours, then burned at 400° C. for 3 hours and controlled again to 10 to 20 mesh to prepare a zirconium dioxide catalyst containing a titanium element (Ti).
Pre-Treatment and Reaction:
The zirconium dioxide catalyst (mole ratio in the catalyst Zr:Ti=98.5:1.5) 7 g prepared above was used to carry out the pre-treatment and the reaction on the same conditions as in Example 14. The reaction results are shown in Table 4.

Example 28

Preparation of Catalyst: Impregnation Method

A zirconium dioxide catalyst (mole ratio in the catalyst Zr:Mg=98.5:1.5) was prepared in the same manner as in Example 15, except that the added element source was changed to 0.362 g of $Mg(NO_3)_2 \cdot 6H_2O$ to add magnesium (Mg) to the catalyst.
Pre-Treatment and Reaction:
The zirconium dioxide catalyst 7 g prepared above was used to carry out the pre-treatment and the reaction on the same conditions as in Example 14. The reaction results are shown in Table 4.

Example 29

Preparation of Catalyst: Impregnation Method

A zirconium dioxide catalyst (mole ratio in the catalyst Zr:Zn=98.5:1.5) was prepared in the same manner as in Example 15, except that the added element source was changed to 0.419 g of $Zn(NO_3)_2 \cdot 6H_2O$ to add zinc (Zn) to the catalyst.
Pre-Treatment and Reaction:
The zirconium dioxide catalyst 7 g prepared above was used to carry out the pre-treatment and the reaction on the same conditions as in Example 14. The reaction results are shown in Table 4.

Example 30

Preparation of Catalyst: Impregnation Method

A zirconium dioxide catalyst (mole ratio in the catalyst Zr:Ca=98.5:1.5) was prepared in the same manner as in Example 15, except that the added element source was changed to 0.333 g of $Ca(NO_3)_2 \cdot 4H_2O$ to add calcium (Ca) to the catalyst.
Pre-Treatment and Reaction:
The zirconium dioxide catalyst 7 g prepared above was used to carry out the pre-treatment and the reaction on the same conditions as in Example 14. The reaction results are shown in Table 4.

Example 31

Preparation of Catalyst: Impregnation Method

A zirconium dioxide catalyst (mole ratio in the catalyst Zr:Fe=98.5:1.5) was prepared in the same manner as in Example 15, except that the added element source was changed to 0.570 g of $Fe(NO_3)_3 \cdot 9H_2O$ to add iron (Fe) to the catalyst.
Pre-Treatment and Reaction:
The zirconium dioxide catalyst 7 g prepared above was used to carry out the pre-treatment and the reaction on the same conditions as in Example 14. The reaction results are shown in Table 4.

Example 32

Preparation of Catalyst: Impregnation Method

A zirconium dioxide catalyst (mole ratio in the catalyst Zr:Pb=98.5:1.5) was prepared in the same manner as in Example 15, except that the added element source was changed to 0.467 g of $Pb(NO_3)_2$ to add lead (Pb) to the catalyst.

Pre-Treatment and Reaction:

The zirconium dioxide catalyst 7 g prepared above was used to carry out the pre-treatment and the reaction on the same conditions as in Example 14. The reaction results are shown in Table 4.

Example 33

Preparation of Catalyst: Impregnation Method

Zirconium hydroxide "XZO 1501/03" manufactured by MEL Chemicals Inc. was molded by compression, and the molded matter was crushed and controlled to 10 to 20 mesh. This zirconium hydroxide 14.6 g (78% by mass in terms of $ZrO_2$) was added to an aqueous solution prepared by dissolving in advance 0.334 g of $Sn(CH_3CO)_2 \cdot H_2O$ (added element source) in 20 g of water by 1 mL of 1N nitric acid, and the mixture was stirred at 50° C. for 30 minutes. Then, water was removed by means of an evaporator, and the residue was dried at 150° C. for 3 hours, then burned at 400° C. for 3 hours and controlled again to 10 to 20 mesh to prepare a zirconium dioxide catalyst containing a tin element (Sn).

Pre-Treatment and Reaction:

The zirconium dioxide catalyst (mole ratio in the catalyst Zr:Sn=98.5:1.5) 7 g prepared above was used to carry out the pre-treatment and the reaction on the same conditions as in Example 14. The reaction results are shown in Table 4.

Example 34

Preparation of Catalyst: Impregnation Method

A zirconium dioxide catalyst (mole ratio in the catalyst Zr:Te=98.5:1.5) was prepared in the same manner as in Example 15, except that the added element source was changed to 0.324 g of $H_6TeO_6$ to add tellurium (Te) to the catalyst.

Pre-Treatment and Reaction:

The zirconium dioxide catalyst 7 g prepared above was used to carry out the pre-treatment and the reaction on the same conditions as in Example 14. The reaction results are shown in Table 4.

Example 35

Preparation of Catalyst: Impregnation Method

A zirconium dioxide catalyst (mole ratio in the catalyst Zr:Cs=98.5:1.5) was prepared in the same manner as in Example 15, except that the added element source was changed to 0.275 g of $CsNO_3$ to add cesium (Cs) to the catalyst.

Pre-Treatment and Reaction:

The zirconium dioxide catalyst 7 g prepared above was used to carry out the pre-treatment and the reaction on the same conditions as in Example 14. The reaction results are shown in Table 4.

Example 36

Preparation of Catalyst: Impregnation Method

Zirconium hydroxide "XZO 1501/03" manufactured by MEL Chemicals Inc. was molded by compression, and the molded matter was crushed and controlled to 10 to 20 mesh. This zirconium hydroxide 14.6 g (78% by mass in terms of $ZrO_2$) was added to an aqueous solution prepared by dissolving in advance 0.165 g of $NH_4VO_3$ (added element source) in 20 g of water by 0.267 g of oxalic acid dihydrate, and the mixture was stirred at 50° C. for 30 minutes. Then, water was removed by means of an evaporator, and the residue was dried at 150° C. for 3 hours, then burned at 400° C. for 3 hours and controlled again to 10 to 20 mesh to prepare a zirconium dioxide catalyst containing a vanadium element (V).

Pre-Treatment and Reaction:

The zirconium dioxide catalyst (mole ratio in the catalyst Zr:V=98.5:1.5) 14 g prepared above was used to carry out the pre-treatment and the reaction on the same conditions as in Example 14. The reaction results are shown in Table 4.

Example 37

Preparation of Catalyst: Impregnation Method

A zirconium dioxide catalyst (mole ratio in the catalyst Zr:Cr=98.5:1.5) was prepared in the same manner as in Example 15, except that the added element source was changed to 0.564 g of $Cr(NO_3)_3 \cdot 9H_2O$ to add chromium (Cr) to the catalyst.

Pre-Treatment and Reaction:

The zirconium dioxide catalyst 7 g prepared above was used to carry out the pre-treatment and the reaction on the same conditions as in Example 14. The reaction results are shown in Table 4.

Example 38

Preparation of Catalyst

Zirconium oxynitrate dihydrate 100 g manufactured by Wako Pure Chemical Industries, Ltd. was dissolved in 800 mL of water, and 1 mL of 1N nitric acid was added thereto. A 25% ammonia aqueous solution was added thereto until a pH of the above solution reached 8 to form a white precipitate. The precipitate was left standing for a night and settled down, and it was subjected to decantation, then filtrated and washed with 600 mL of water. After dried at 150° C. for 3 hours, this was burned at 400° C. for 3 hours, crushed and then controlled to 10 to 20 mesh to prepare a zirconium dioxide catalyst.

Pre-Treatment and Reaction:

The zirconium dioxide catalyst 7 g prepared above by a precipitation method was used to carry out the pre-treatment and the reaction on the same conditions as in Example 14. The reaction results are shown in Table 4.

Example 39

Preparation of Catalyst: Coprecipitation Method

Zirconium oxynitrate dihydrate 100 g and lanthanum nitrate hexahydrate 8.53 g manufactured by Wako Pure Chemical Industries, Ltd. were dissolved in 800 mL of water, and 1 mL of 1N nitric acid was added thereto. A 25% ammonia aqueous solution was added thereto until a pH of the above solution reached 8 to form a white precipitate. The precipitate was left standing for a night and settled down, and it was subjected to decantation, then filtrated and washed with 600 mL of water. After dried at 150° C. for 3 hours, this was burned at 400° C. for 3 hours, crushed and then controlled to 10 to 20 mesh to prepare a zirconium dioxide catalyst containing a lanthanum element (La).

Pre-Treatment and Reaction:

The zirconium dioxide catalyst (mole ratio in the catalyst Zr:La=98:2) 7 g prepared above was used to carry out the pre-treatment and the reaction on the same conditions as in Example 14. The reaction results are shown in Table 4.

analyzed by means of a gas chromatography to find that a conversion rate of α-hydroxyisobutyroamide was 95% and that a selectivity of methyl α-hydroxyisobutyrate was 92%. The reaction was continued to find that a conversion rate of

TABLE 4

| | | Reaction temperture (° C.) | Reaction pressure (kPa) | Catalyst | WHSV based on α-hydroxy-carboxylic amide (hr$^{-1}$) | Reaction results | | Time for which conversion rate of 90% or more could be maintained (hr) |
|---|---|---|---|---|---|---|---|---|
| | | | | | | After 24 hours | | |
| | | | | | | Conversion rate (%) | Selectivity (%) | |
| Example | 14 | 220 | 101.3 | XZO 1501/03 | 0.3 | 94 | 89 | 120 |
| | 15 | 220 | 101.3 | XZO 1501/03 (Zr) | 0.3 | 94 | 85 | 120 |
| | 16 | 220 | 101.3 | XZO 1501/03 (Y) | 0.3 | 95 | 90 | 804 |
| | 17 | 220 | 101.3 | XZO 1501/03 (La) | 0.3 | 95 | 88 | 720 |
| | 18 | 220 | 101.3 | XZO 1501/03 (Co) | 0.3 | 95 | 87 | 671 |
| | 19 | 220 | 101.3 | XZO 1501/03 (Mn) | 0.3 | 94 | 87 | 660 |
| | 20 | 220 | 101.3 | XZO 1501/03 (Ni) | 0.3 | 95 | 89 | 622 |
| | 21 | 220 | 101.3 | XZO 1501/03 (Yb) | 0.3 | 95 | 89 | 456 |
| | 22 | 220 | 101.3 | XZO 1501/03 (Al) | 0.3 | 94 | 90 | 454 |
| | 23 | 220 | 101.3 | XZO 1501/03 (B) | 0.3 | 95 | 87 | 420 |
| | 24 | 220 | 101.3 | XZO 1501/03 (Cu) | 0.3 | 95 | 88 | 336 |
| | 25 | 220 | 101.3 | XZO 1501/03 (Ce) | 0.3 | 94 | 89 | 335 |
| | 26 | 220 | 101.3 | XZO 1501/03 (Bi) | 0.3 | 94 | 87 | 297 |
| | 27 | 220 | 101.3 | XZO 1501/03 (Ti) | 0.3 | 95 | 88 | 224 |
| | 28 | 220 | 101.3 | XZO 1501/03 (Mg) | 0.3 | 94 | 91 | 190 |

TABLE 5

| | | Reaction temperture (° C.) | Reaction pressure (kPa) | Catalyst | WHSV based on α-hydroxy-carboxylic amide (hr$^{-1}$) | Reaction results | | Time for which conversion rate of 90% or more could be maintained (hr) |
|---|---|---|---|---|---|---|---|---|
| | | | | | | After 24 hours | | |
| | | | | | | Conversion rate (%) | Selectivity (%) | |
| Example | 29 | 220 | 101.3 | XZO 1501/03 (Zn) | 0.3 | 94 | 91 | 169 |
| | 30 | 220 | 101.3 | XZO 1501/03 (Ca) | 0.3 | 95 | 89 | 153 |
| | 31 | 220 | 101.3 | XZO 1501/03 (Fe) | 0.3 | 94 | 91 | 144 |
| | 32 | 220 | 101.3 | XZO 1501/03 (Pb) | 0.3 | 94 | 90 | 122 |
| | 33 | 220 | 101.3 | XZO 1501/03 (Sn) | 0.3 | 94 | 89 | 106 |
| | 34 | 220 | 101.3 | XZO 1501/03 (Te) | 0.3 | 94 | 88 | 74 |
| | 35 | 220 | 101.3 | XZO 1501/03 (Cs) | 0.3 | 94 | 89 | 46 |
| | 36 | 220 | 101.3 | XZO 1501/03 (V) | 0.3 | 92 | 89 | 35 |
| | 37 | 220 | 101.3 | XZO 1501/03 (Cr) | 0.3 | 92 | 90 | 35 |
| | 38 | 220 | 101.3 | Zirconium dioxide obtained by precipitation method | 0.3 | 75 | 87 | 0 |
| | 39 | 220 | 101.3 | Zirconium dioxide obtained by coprecipitation method | 0.3 | 94 | 87 | 167 |

Example 40

The catalyst was prepared at a burning temperature changed to 500° C. in Example 16, and the pre-treatment and the reaction were carried out on the same conditions, except that a use amount of the catalyst was changed to 4.2 g (WHSV based on α-hydroxyisobutyroamide=0.5 hr$^{-1}$) and that the reaction temperature was changed to 210° C.

When the reaction reached a steady state after about 24 hours passed, the products were sampled in an ice trap and α-hydroxyisobutyroamide could be maintained at 90% or more for 216 hours since starting the reaction.

Example 41

The pre-treatment and the reaction were carried out on the same conditions, except that in Example 40, a content ratio (mole ratio) of yttrium (Y) in the catalyst was controlled so that it was Zr:Y=94:6. The catalyst thus obtained was analyzed by means of a fluorescent X ray analytical equipment "SEA2010" (manufactured by SEICO Electronics Industrial Co., Ltd.) to find that an intensity ratio (Y/Zr) obtained was 0.074.

When the reaction reached a steady state after about 24 hours passed, the products were sampled in an ice trap and analyzed by means of a gas chromatography to find that a conversion rate of α-hydroxyisobutyroamide was 94% and that a selectivity of methyl α-hydroxyisobutyrate was 92%. The reaction was continued to find that a conversion rate of α-hydroxyisobutyroamide could be maintained at 90% or more for 360 hours since starting the reaction.

Example 42

Preparation of Catalyst

Water 500 g was added to 30.6 g of zirconium hydroxide "XZO 1501/03" manufactured by MEL Chemicals Inc. to prepare a slurry, and it was heated at 50 to 60° C. while stirring. An aqueous solution prepared by dissolving in advance 3.9 g of Y(CH$_3$COO)$_3$.4H$_2$O in 100 g of water and heated at 50° C. was added thereto and stirred at 50 to 60° C. for 1 hour. The above addition amount corresponds to Zr:Y=94:6 which is a content ratio (mole ratio) of yttrium (Y) in the catalyst. The solution was cooled down to room temperature and then controlled to pH 8.0 by a 25% ammonia aqueous solution, and it was further stirred for 30 minutes and left standing for about 16 hours to precipitate zirconium hydroxide. The supernatant was removed, and 300 g of water was added thereto. The mixture was stirred again for 30 minutes in a slurry state and left standing for about 3 hours to precipitate zirconium hydroxide, and the precipitate was washed with water after removing the supernatant. A precipitate of zirconium hydroxide obtained by carrying out once again the same washing with water and then removing the supernatant was dried by heating gradually up to 150° C. in 72 hours in a dryer. This was molded by compression, and the molded matter was crushed and controlled to 10 to 20 mesh. This was dried at 150° C. for 3 hours, then burned at 400° C. for 3 hours and controlled again to 10 to 20 mesh to prepare a zirconium dioxide catalyst. The catalyst thus obtained was analyzed by means of the fluorescent X ray analytical equipment "SEA2010" (manufactured by SEICO Electronics Industrial Co., Ltd.) to find that an intensity ratio (Y/Zr) obtained was 0.069 and that it was almost the same value as that of the catalyst prepared in Example 40.

Pre-Treatment and Reaction:

The zirconium dioxide catalyst (mole ratio in the catalyst Zr:Y=94:6) 4.2 g prepared above was used to carry out the pre-treatment and the reaction on the same conditions as in Example 40.

When the reaction reached a steady state after about 24 hours passed, the products were sampled in an ice trap and analyzed by means of a gas chromatography to find that a conversion rate of α-hydroxyisobutyroamide was 94% and that a selectivity of methyl α-hydroxyisobutyrate was 92%. The reaction was continued to find that a conversion rate of α-hydroxyisobutyroamide could be maintained at 90% or more for 793 hours since starting the reaction.

Example 43

The pre-treatment and the reaction were carried out on the same conditions, except that in Example 42, a content ratio (mole ratio) of yttrium (Y) in the catalyst was controlled so that it was Zr:Y=96:4.

When the reaction reached a steady state after about 24 hours passed, the products were sampled in an ice trap and analyzed by means of a gas chromatography to find that a conversion rate of α-hydroxyisobutyroamide was 94% and that a selectivity of methyl α-hydroxyisobutyrate was 91%. The reaction was continued to find that a conversion rate of α-hydroxyisobutyroamide could be maintained at 90% or more for 699 hours since starting the reaction.

Example 44

The pre-treatment and the reaction were carried out on the same conditions, except that in Example 42, a content ratio (mole ratio) of yttrium (Y) in the catalyst was controlled so that it was Zr:Y=91:9.

When the reaction reached a steady state after about 24 hours passed, the products were sampled in an ice trap and analyzed by means of a gas chromatography to find that a conversion rate of α-hydroxyisobutyroamide was 94% and that a selectivity of methyl α-hydroxyisobutyrate was 93%. The reaction was continued to find that a conversion rate of α-hydroxyisobutyroamide could be maintained at 90% or more for 194 hours since starting the reaction.

Example 45

Preparation of Catalyst

A catalyst was prepared on the same conditions, except that in Example 42, the amounts of the reagents and water used were increased to 13 times respectively.

Pre-Treatment:

A SUS316-made reaction tube having an inner diameter of 28 mmφ was charged with 200 g of the zirconium dioxide catalyst prepared above. The reaction tube was heated by a heat transfer oil while allowing nitrogen to flow at 100 ml/minute, and the zirconium dioxide catalyst charged was heated at 80° C. After stopping supplying of nitrogen, methanol was allowed to pass through the reaction tube at 190 g/hour, and after methanol came out from an outlet of the reaction tube, the catalyst was heated up to 210° C.

Reaction:

After stopping supplying of methanol, a raw material liquid prepared by mixing α-hydroxyisobutyroamide and methanol in a proportion of 30 parts by mass to 70 parts by mass was allowed to flow through the reaction tube at a flow rate of 200 g/hour (WHSV based on α-hydroxyisobutyroamide=0.3 hr$^{-1}$) while controlling a temperature of the catalyst layer at 210° C.

When the reaction reached a steady state after 29 hours passed, the products were cooled by water, sampled and analyzed by means of a gas chromatography to find that a conversion rate of α-hydroxyisobutyroamide was 94% and that a selectivity of methyl α-hydroxyisobutyrate was 91%. The reaction was continued to find that after 143 hours passed, a conversion rate of α-hydroxyisobutyroamide was 94% and that a selectivity of methyl α-hydroxyisobutyrate was 94%. Further, the reaction liquid cooled by water was dissolved in water and quantitatively determined in terms of an ammonium ion by means of a capillary electrophoretic equipment "G1600A" (manufactured by Agilent Technologies Inc.) to find that an ammonia selectivity based on α-hydroxyisobutyroamide was 94%.

Refining by Distillation:

The reaction gas after 143 hours passed since the reaction described above started was supplied to a middle stage of a distillation column obtained by filling a glass tube having an inner diameter of 28 mm with 500 mm of irregular filler 6 mm MacMahon packings and continuously distilled. The conditions were controlled to a column top temperature of 60 to 62° C. and a column bottom liquid temperature of 75 to 85° C.

while maintain a reflux ratio at about 3, and taken out were a distillate at 99 g/hour and a bottom product at 100 g/hour.

The composition of the bottom product (column bottom liquid) was methanol/methyl α-hydroxyisobutyrate/α-hydroxyisobutyroamide=30/65/4 (mass ratio). A mass ratio of a holdup amount of the bottom part liquid to the bottom product amount per hour was 1. An ammonia amount in the bottom product was 111 ppm, and an amount of methyl α-hydroxyisobutyrate contained in distilled methanol was 150 ppm.

Methyl α-hydroxyisobutyrate was isolated from the above bottom product and refined by a conventional distillation operation.

Example 46

The pre-treatment and the reaction were carried out on the same conditions, except that in Example 3, the raw materials were changed so that a mixed solution comprising 10 parts by mass of lactoamide and 90 parts by mass of methanol was supplied at 8.8 g/hour and that they were carried out at a temperature (reaction temperature) of 230° C. in the catalyst layer.

The reaction results after about 24 hours passed were that a conversion rate of lactoamide was 90% and that a selectivity of methyl lactate was 85%.

INDUSTRIAL APPLICABILITY

The α-hydroxycarboxylic esters obtained by the production process of the present invention are important compounds used for various industrial applications, and in a case of, for example, lactic esters, they are used as high boiling solvents and in addition thereto, used as raw materials for food additives, fragrances, medicines & agricultural chemicals and biodegradable polymers. In particular, α-hydroxyisobutyric esters are used as raw materials for solvents and medicines & agricultural chemicals, and in addition thereto, they are used as well for synthesis of methacrylic esters, particularly, methyl methacrylate and also used as synthetic raw materials for α-amino acids by aminolysis.

The invention claimed is:

1. A process of producing an α-hydroxycarboxylic ester, the process comprising:
reacting in a gas phase an α-hydroxycarboxylic amide and an aliphatic alcohol in the presence of a zirconium dioxide catalyst.

2. The process of claim 1, wherein the zirconium dioxide catalyst comprises at least one element selected from the group consisting of a 2nd to a 4th group element, a 7th group element, a 9th to a 13th group element, lanthanoid, antimony (Sb) and bismuth (Bi).

3. The of claim 1, wherein the zirconium dioxide catalyst comprises at least one element selected from the group consisting of boron (B), aluminum (Al), manganese (Mn), cobalt (Co), nickel (Ni), yttrium (Y), lanthanum (La) and ytterbium (Yb).

4. The process of claim 1, wherein the α-hydroxycarboxylic amide has a Formula (I):

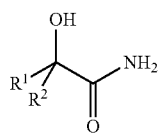

(I)

wherein $R^1$ and $R^2$ each represent independently a hydrogen atom, an alkyl group comprising 1 to 20 carbon atoms, an alkenyl group comprising 2 to 20 carbon atoms or a cycloalkyl group comprising 3 to 20 ring-forming carbon atoms, and
wherein the aliphatic alcohol has a Formula (II):

$R^3OH$ (II)

wherein $R^3$ is an alkyl group comprising 1 to 20 carbon atoms, an alkenyl group comprising 2 to 20 carbon atoms or a cycloalkyl group comprising 3 to 20 ring-forming carbon atoms.

5. The process of claim 1, wherein the α-hydroxycarboxylic amide is lactoamide or α-hydroxyisobutyroamide.

6. The process of claim 1, wherein the aliphatic alcohol is methanol or ethanol.

7. The process of claim 1, wherein a reaction temperature is 150 to 270° C., and a reaction pressure is 1 to 300 kPa.

8. The process of claim 2, wherein the α-hydroxycarboxylic amide has a Formula (I):

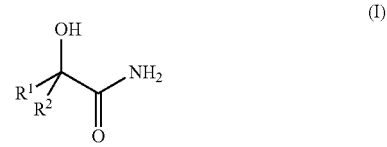

(I)

wherein $R^1$ and $R^2$ each represent independently a hydrogen atom, an alkyl group comprising 1 to 20 carbon atoms, an alkenyl group comprising 2 to 20 carbon atoms or a cycloalkyl group comprising 3 to 20 ring-forming carbon atoms, and wherein the aliphatic alcohol has a Formula (II):

$R^3OH$ (II)

wherein $R^3$ is an alkyl group comprising 1 to 20 carbon atoms, an alkenyl group comprising 2 to 20 carbon atoms or a cycloalkyl group comprising 3 to 20 ring-forming carbon atoms.

9. The process of claim 3, wherein the α-hydroxycarboxylic amide Formula (I):

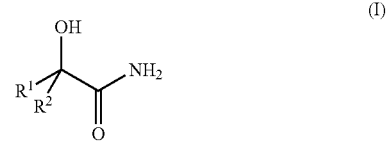

(I)

wherein $R^1$ and $R^2$ each represent independently a hydrogen atom, an alkyl group comprising 1 to 20 carbon atoms, an alkenyl group comprising 2 to 20 carbon atoms or a cycloalkyl group comprising 3 to 20 ring-forming carbon atoms, and
wherein the aliphatic alcohol has a Formula (II):

$R^3OH$ (II)

wherein $R^3$ is an alkyl group comprising 1 to 20 carbon atoms, an alkenyl group comprising 2 to 20 carbon atoms or a cycloalkyl group comprising 3 to 20 ring-forming carbon atoms.

10. The process of claim 2, wherein the α-hydroxycarboxylic amide is lactoamide or α-hydroxyisobutyroamide.

11. The process of claim 3, wherein the α-hydroxycarboxylic amide is lactoamide or α-hydroxyisobutyroamide.

12. The process of claim 2, wherein the aliphatic alcohol is methanol or ethanol.

13. The process of claim 3, wherein the aliphatic alcohol is methanol or ethanol.

14. The process of claim 4, wherein the aliphatic alcohol is methanol or ethanol.

15. The process of claim 5, wherein the aliphatic alcohol is methanol or ethanol.

16. The process of claim 2, wherein a reaction temperature is 150 to 270° C., and a reaction pressure is 1 to 300 kPa.

17. The process of claim 3, wherein a reaction temperature is 150 to 270° C., and a reaction pressure is 1 to 300 kPa.

18. The process of claim 4, wherein a reaction temperature is 150 to 270° C., and a reaction pressure is 1 to 300 kPa.

19. The process of claim 5, wherein a reaction temperature is 150 to 270° C., and a reaction pressure is 1 to 300 kPa.

20. The process of claim 6, wherein a reaction temperature is 150 to 270° C., and a reaction pressure is 1 to 300 kPa.

* * * * *